(12) United States Patent
Jansson

(10) Patent No.: US 6,875,869 B2
(45) Date of Patent: Apr. 5, 2005

(54) PROCESS FOR THE MANUFACTURE OF QUINOLINE DERIVATIVES

(75) Inventor: Karl Jansson, Dalby (SE)

(73) Assignee: Active Biotech AB, Lund (SE)

( * ) Notice: Subject to any disclaimer, the term of this patent is extended or adjusted under 35 U.S.C. 154(b) by 118 days.

(21) Appl. No.: 10/459,718

(22) Filed: Jun. 12, 2003

(65) Prior Publication Data

US 2004/0034227 A1 Feb. 19, 2004

Related U.S. Application Data

(60) Provisional application No. 60/387,580, filed on Jun. 12, 2002.

(51) Int. Cl.[7] .................... C07D 491/00; C07D 498/00; C07D 515/00; C07D 215/16; C07D 215/20
(52) U.S. Cl. ......................................... 546/90; 546/155
(58) Field of Search ................................... 546/90, 155

(56) References Cited

U.S. PATENT DOCUMENTS

| | | | |
|---|---|---|---|
| 4,738,971 A | 4/1988 | Eriksoo et al. | |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |

*Primary Examiner*—Richard L. Raymond
*Assistant Examiner*—Zachary C. Tucker
(74) *Attorney, Agent, or Firm*—Browdy and Neimark, P.L.L.C.

(57) ABSTRACT

A process for the preparation of the compounds of general formula (I)

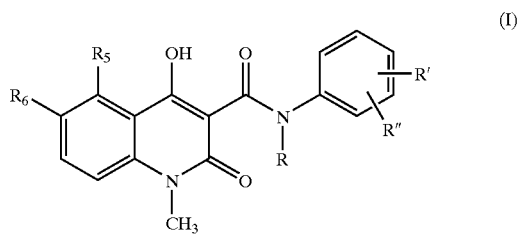

(I)

wherein R is selected from methyl, ethyl, n-propyl, iso-propyl, n-butyl, iso-butyl, sec.-butyl and allyl; $R_5$ is selected from the methyl, ethyl, n-propyl, iso-propyl, methoxy, ethoxy, methylthio, ethylthio, n-propylthio, methylsulphinyl, ethylsulphinyl, fluoro, chloro, bromo, trifluoromethyl, and $OCH_xF_y$; wherein x=0–2, y=1–3 with the proviso that x+y=3; $R_6$ is hydrogen; or $R_5$ and $R_6$ taken together are methylenedioxy; R' is selected from methyl, methoxy, fluoro, chloro, bromo, trifluoromethyl, and $OCH_xF_y$, wherein x=0–2, y=1–3 with the proviso that x+y=3; R" is selected form hydrogen, fluoro and chloro, with the proviso that R" is selected from fluoro and chloro only when R' is selected from fluoro and chloro; by reacting a quinoline-3-carboxylic acid ester derivative of formula A with an aniline derivative of formula B

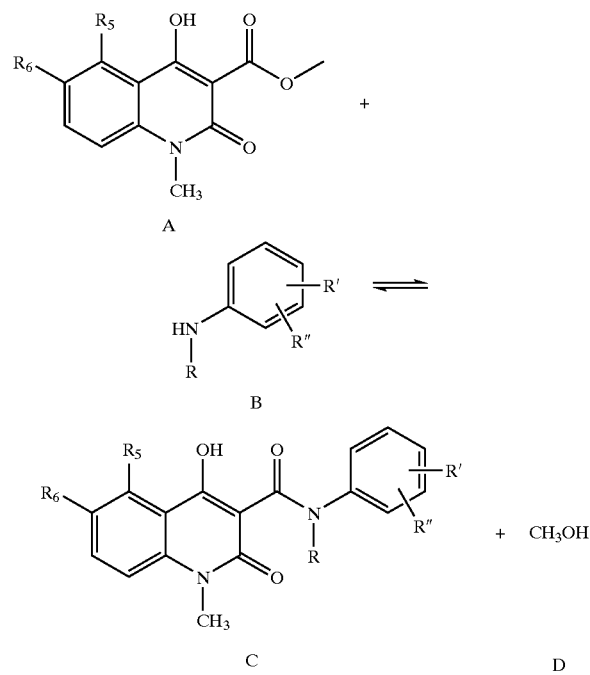

in a solvent selected from straight or branched alkanes and cycloalkanes or mixtures thereof with a boiling point between 80 and 200° C.

6 Claims, No Drawings

PROCESS FOR THE MANUFACTURE OF QUINOLINE DERIVATIVES

FIELD OF THE INVENTION

The present invention relates to a process for the manufacturing of quinoline derivatives. More particularly, the present invention relates to an improved and simplified process for the manufacture of quinoline-3-carboxamide derivatives.

BACKGROUND OF THE INVENTION

In U.S. Pat. No. 4,738,971 some derivatives of N-aryl-1,2-dihydro-4-substituted-1-alkyl-2-oxo-quinoline-3-carboxamide are claimed as enhancers of cell-mediated immunity. Said patent discloses four methods for the preparation of the compounds. According to the method closest to that of the present invention, the compounds are prepared by reacting a carboxylic acid or a reactive derivative thereof with an amine or reactive derivative thereof in the presence of pyridine or quinoline as an inert solvent. U.S. Pat. No. 5,912,349 discloses an improved process to produce one of these compounds, roquinimex (Merck Index 12th Ed., No. 8418; Linomide®, LS2616, N-phenyl-N-methyl-1,2-dihydro-4-hydroxy-1-methyl-2-oxo-quinoline3-carboxamide). In said patent a reaction between N-methylisatoic anhydride and N-methyl-N-phenyl-α-carbomethoxyacetamide gives the desired compound. U.S. Pat. Nos. 6,077,851, 6,133,285 and 6,121,287 disclose the preparation of quinoline-3-carboxamide derivatives. The derivatives may be prepared by various known methods, for example, by reaction of a quinoline-3-carboxylic acid ester derivative with an aniline in a suitable solvent such as toluene, xylene and the like. In the examples disclosed, wherein toluene is used as a solvent, the yields are ≦80%.

The prior art reaction disclosed below

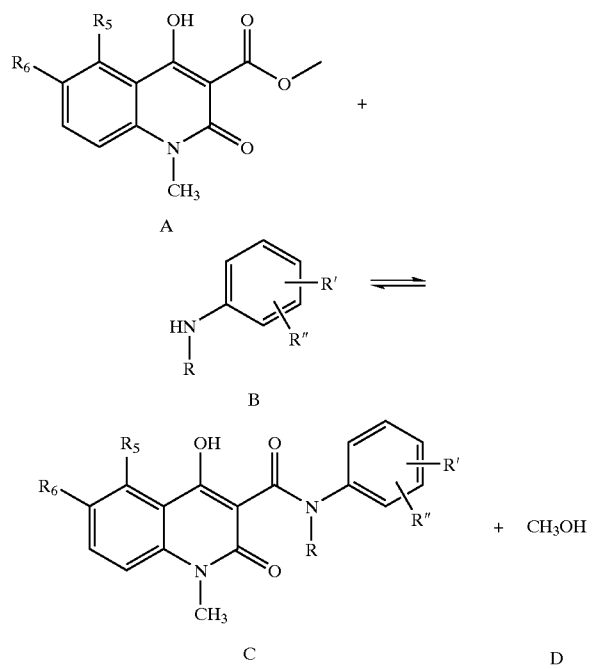

showing the N-acylation reaction conducted with a quinoline-3-carboxylic acid ester derivative has now been found to be an equilibrium reaction where the equilibrium point unexpectedly lies far to the left. An illustrative example is provided by heating a quinoline-3-carboxamide derivative (compound C), for example, wherein $R_5$=chloro and $R_6$=H, R=ethyl and R'=R"=hydrogen, in a sealed vessel at 100° C. with one equivalent of methanol in toluene as a solvent. An almost complete transformation into the corresponding methyl ester (compound A) results after less than 30 minutes.

The chemical stability of the desired product is such that degradation occurs under the reaction conditions.

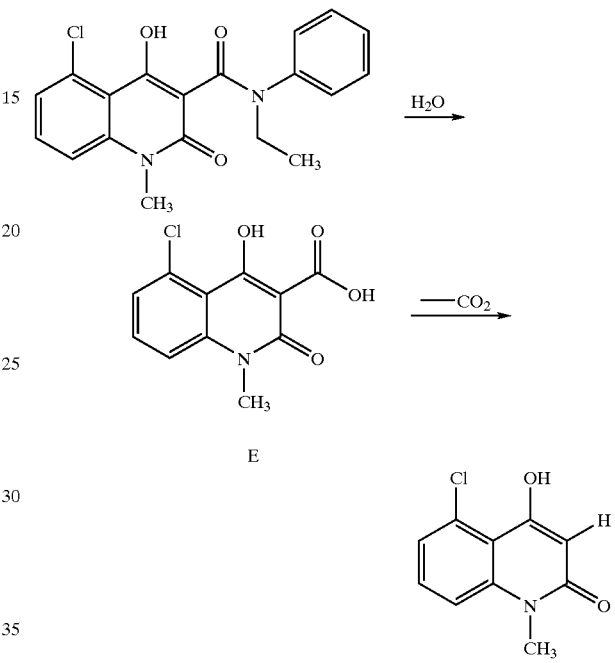

Degradation of a quinoline-3-carboxamide derivative.

An illustrative example is provided above. The degradation product (compound F) is the decarboxylated quinoline-3-carboxylic acid (compound E). Compound E is formed from the reaction between the quinoline-3-carboxamide derivative and water. It is unavoidable that small amounts of water exist in a reaction mixture. Small amounts of water are always present in the starting materials and in the solvent and water can also enter the reaction mixture during the reaction. When using, for example, toluene, the desired product is dissolved and prone to reaction with water. The quinoline-3-carboxylic acid that is formed in the reaction between the quinoline-3-carboxamide derivative and water undergoes a decarboxylation reaction to yield the decarboxylated product (compound F). The quinoline-3-carboxylic acid is not present in the crude product in a detectable amount. The quinoline-3-carboxylic acid ester (compound A) also undergoes a similar reaction with water but at a much slower rate.

DESCRIPTION OF THE INVENTION

A primary objective of the present invention is to provide an improved process for the manufacturing of quinoline-3-carboxamide derivatives which by virtue of their pharmacological profile, with high activity and low side-effects, are considered to be of value in the treatment of disease resulting from pathologic inflammation and autoimmunity and the treatment of a plurality of malignant tumours. More particularly, the present invention relates to a greatly simplified process for the manufacture of a quinoline-3-carboxamide derivative from an aniline by a N-acylation reaction conducted with a quinoline-3-carboxylic acid ester derivative in order to improve yield and chemical purity of the desired product.

It has now surprisingly been found that the compounds of general formula (I)

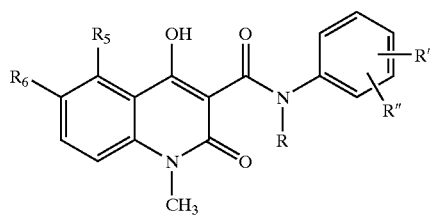

(I)

wherein

R is selected from methyl, ethyl, n-propyl, iso-propyl, n-butyl, iso-butyl, sec.-butyl and allyl;

$R_5$ is selected from methyl, ethyl, n-propyl, iso-propyl, methoxy, ethoxy, methylthio, ethylthio, n-propylthio, methylsulphinyl, ethylsulphinyl, fluoro, chloro, bromo, trifluoromethyl, and $OCH_xF_y$;

wherein x=0–2, y=1–3 with the proviso that x+y=3;

$R_6$ is hydrogen; or $R_5$ and $R_6$ taken together are methylenedioxy;

R' is selected from methyl, methoxy, fluoro, chloro, bromo, trifluoromethyl, and $OCH_xF_y$, wherein x=0–2, y=1–3 with the proviso that x+y=3;

R" is selected from hydrogen, fluoro and chloro, with the proviso that R" is selected from fluoro and chloro only when R' is selected from fluoro and chloro;

by the claimed process comprising reacting a quinoline-3-carboxylic acid ester derivative of formula A with an aniline derivative of formula B

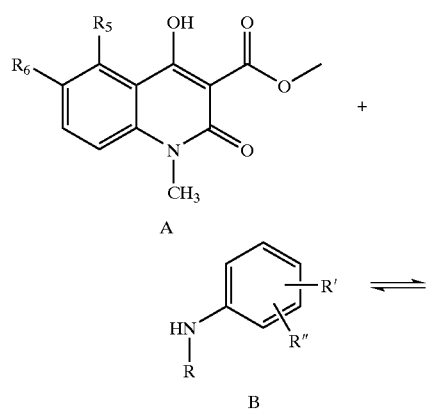

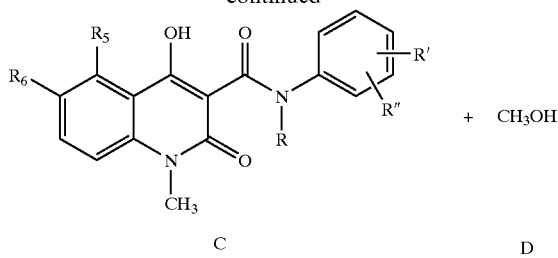

in a solvent selected from straight or branched alkanes and cycloalkanes or mixtures thereof with a boiling point between 80 and 200° C. are manufactured in a greatly improved and simplified way.

According to a preferred embodiment the solvent is n-heptane, n-octane or mixtures thereof In a further preferred embodiment the solvent is cis,trans-decahydronaphthalene (Decalin®).

The process according to the invention is especially preferred for the preparation of N-ethyl-phenyl-5-chloro-1,2-dihydro-4-hydroxy-1-methyl-2-oxo-quinoline-3-carboxamide using n-heptane as a solvent; for the preparation of N-methyl-N-(4-trifluoromethyl-phenyl)-1,2-dihydro-4-hydroxy-5-methoxy-1-methyl-2oxo-quinoline-3-carboxamide using a mixture of n-heptane and n-octane as a solvent; for the preparation of N-ethyl-N-phenyl-1,2-dihydro-5-ethyl-4-hydroxy-1-methyl-2-oxo-quinoline-3-carboxamide using cis,trans-decahydronaphthalene as a solvent.

In relation to the use of toluene, xylene and the like as solvents, it has now surprisingly and unexpectedly been found that yield and impurity profile of the desired products can be very much improved. By using a solvent wherein the desired product is in effect insoluble even at reflux temperature, combined with removal of the alcohol formed, the yield of the desired product is almost 100% with a very low level of impurities in the desired product. Precipitation of the desired product increases the reaction rate even further, and prevents the degradation, i.e., by avoiding the reaction of the desired product with water. Solvents improving the process are straight- or branch-chained alkanes and cycloalkanes or mixtures thereof with a boiling point between 80 and 200° C. Reduced pressure may be used to remove the alcohol formed.

EXAMPLES

Without further elaboration, it is believed that one skilled in the art, using the preceding description, practice the present invention to its fullest extent. The following detailed examples describe how to prepare the various compounds and/or perform the various processes of the invention and are to be considered as merely illustrative, and not limitations of the preceding disclosure in any way whatsoever.

Example 1

1,2-Dihydro-4-hydroxy-5-chloro-1-methyl-2-oxo-quinoline-3-carboxylic acid methyl ester 2-Amino-6-chlorobenzoic acid (30 g) was suspended in 1,4-dioxane (225 ml) and ethyl chloroformate (75 ml) was added. The mixture was heated at reflux for 1 hour, then cooled to 50° C. and acetyl chloride (75 ml) was added. The mixture was stirred for 10 hours, after which the precipitated product was filtered off and washed with toluene. Drying in vacuum yields 5-chloroisatoic anhydride (33 g, 97% yield). 5-Chloroisatoic anhydride (30 gram) was dissolved in dimethylacetamide (300 ml), and cooled to 5° C. over a nitrogen atmosphere. Sodium hydride (5.8 g, 70%) was added portionwise, followed by addition of methyl iodide (11.5 ml). The reaction mixture was stirred at room temperature for 18 hours and the evacuated (40 mbar) for 1 hour in order to remove excess methyl iodide. Sodium hydride (5.8 g, 70%) was added followed by addition of dimethyl malonate (20 ml), and the mixture was heated to 85° C. After 3 hours at 85° C., the mixture was cooled and diluted with cold water (2.4 litre). The product was precipitated by addition of 5 M HCl (aq) until pH=1.5–2. Filtration of the precipitated product and recrystallisation from methanol gave the title compound (29 g, 70% yield).

In essentially the same manner the ethyl ester is obtained from the corresponding starting materials.

Example 2
N-Ethyl-N-phenyl-5-chloro-1,2-dihydro-4-hydroxy-1-methyl-2-oxo-quinoline-3-carboxamide 5-Chloro-1,2-dihydro-4-hydroxy-1-methyl-2-oxo-quinoline-3-carboxylic acid methyl ester (3.0 g), N-ethylaniline (2 eq 2–2.88 ml), and heptaue (60 ml) were heated and the volatiles, mainly heptane and formed methanol, (32 ml) distilled off during 6 hours and 35 minutes. After cooling to room temperature the crystalline suspension was filtered and the crystals were washed with heptane and dried in vacuum to yield the crude title compound (3.94 g, 98%) as white to off-white crystals.

Example 3
N-Ethyl-N-phenyl-5-chloro-1,2-dihydro-4hydroxy-1-methyl-2-oxo-quinoline-3-carboxamide (reaction in toluene not part of the invention)

5-Chloro-1,2-dihydro-4-hydroxy-1-methyl-2-oxo-quinoline-3-carboxylic acid methyl ester (3.0 g), N-ethylaniline (2 eq. 2.88 ml), and toluene (60 ml) were heated and the volatiles, mainly toluene and formed methanol, (32 ml) were distilled off during 6 hours and 35 minutes. After cooling to room temperature and precipitation of the product with heptane (40 ml), the crystals were filtered and washed with heptane and dried in vacuum to yield the crude title compound (3.58 g. 90% yield) as off-white crystals.

The crude products were analysed using HPLC and reference compounds, see table 1. Only two by-products were detected in the crude products. Peaks with area-% below 0.02% are not included.

The increased reaction rate in heptane is apparent. More untransformed ester remained in the crude product when using toluene as compared to heptane as a solvent. The rate difference may be even bigger than indicated in Table 1 since reaction in toluene occurs at a higher temperature than the corresponding reaction in heptane (toluene has bp 110–112° C. and heptane has bp 98° C.) The ester is more soluble in alkanes than the product, a fact that influences the equilibrium positively and favours formation of product.

The yield of crude product when using toluene wags lower (90%) than when using heptane (98%). This can be attributed to the higher solubility of product and ester in toluene than in heptane. The actual yield when using heptane is close to 100% The decarboxylated quinoline carboxylic acid (toluene 0.54%, and heptane 0.03%, see Table 1) is the result of reaction between water and the desired product.

I claim:
1. A process for the preparation of the compounds of general formula (I)

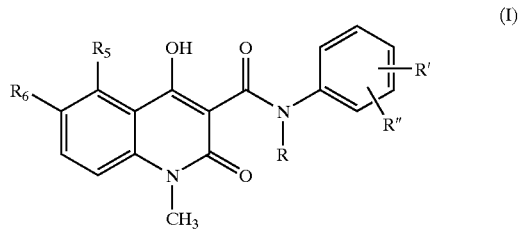

wherein

R is selected from methyl, ethyl, n-propyl, iso-propyl, n-butyl, iso-butyl, sec.-butyl and allyl;

$R_5$ is selected from methyl, ethyl, n-propyl, iso-propyl, methoxy, ethoxy, methylthio, ethylthio, n-propylthio, methylsulphinyl, ethylsulphinyl, fluoro, chloro, bromo, trifluoromethyl, and $OCH_xF_y$;

wherein
x=0–2,
y=1–3 with the proviso that
x+y=3;

$R_6$ is hydrogen; or $R_5$ and $R_6$ taken together are methylenedioxy;

R' is selected from methyl, methoxy, fluoro, chloro, bromo, trifluoromethyl, and $OCH_xF_y$,

TABLE 1

Content of desired product and by-products in the crude products

| | weight-% in crude product (N-Ethyl-N-phenyl carboxamide product) | weight-% in crude product (methyl ester) | weight-% in crude product (decarboxylated quinoline) |
|---|---|---|---|
| Heptane as solvent | 99.4 | 0.02 | 0.03 |
| Toluene as solvent | 94.0 | 4.55 | 0.54 | wherein
x=0–2,
y=1–3 with the proviso that
x+y=3;
R″ is selected from hydrogen, fluoro and chloro, with the proviso that R″ is selected from flouro and chloro only when R' is selected from flouro and chloro;
by reacting a quinoline-3-carboxylic acid ester derivative of formula A with an aniline derivative of formula B according to the following reaction diagram, to give the compound of general formula (I), designated "C", and methanol, designated "D":

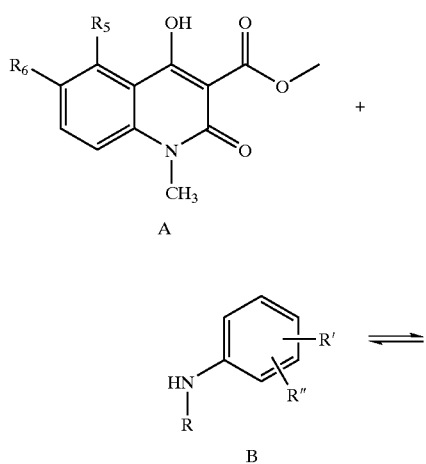

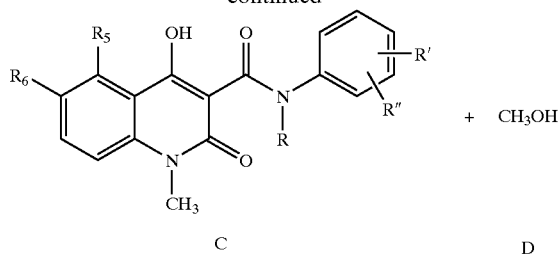

in a solvent selected from straight or branched alkanes and cycloalkanes or mixtures thereof with a boiling point between 80 and 200° C.

2. The process according to claim 1 wherein the solvent is n-heptane, n-octane or mixtures thereof.

3. The process according to claim 1 wherein the solvent is cis,trans-decahydronaphthalene.

4. The process according to claim 1 for the preparation of N-ethyl-N-phenyl-5-chloro-1,2-dihydro-4-hydroxy-1-methyl-2-oxo-quinoline-3-carboxamide using n-heptane as a solvent.

5. The process according to claim 1 for the preparation of N-methyl-N-(4-trifluoromethyl-phenyl)-1,2-dihydro-4-hydroxy-5-methoxy-1-methyl-2-oxo-quinoline-3-carboxamide using a mixture of n-heptane and n-octane as a solvent.

6. The process according to claim 1 for the preparation of N-ethyl-N-phenyl-1,2-dihydro-5-ethyl-4-hydroxy-1-methyl-2-oxo-quinoline-3-carboxamide using cis,trans-decahydro-naphthalene as a solvent.

* * * * *